(12) United States Patent
Nieboer et al.

(10) Patent No.: US 6,410,259 B1
(45) Date of Patent: Jun. 25, 2002

(54) PROCESS FOR THE FERMENTATIVE PRODUCTION OF DEACYLATED CEPHALOSPORINS

(75) Inventors: Maarten Nieboer, Berkel en Rodenrijs; Erik De Vroom, Leiden; Johannis Lugtenburg, Oegstgeest; Dirk Schipper, Delft; Adrianus Wilhelmus Hermanus Vollebregt, Naaldwijk; Roelof Ary Lans Bovenberg, Rotterdam, all of (NL)

(73) Assignee: DSM Patents & Trademarks, Ma Delft (NL)

( * ) Notice: Subject to any disclaimer, the term of this patent is extended or adjusted under 35 U.S.C. 154(b) by 0 days.

(21) Appl. No.: 09/202,797

(22) PCT Filed: Apr. 22, 1998

(86) PCT No.: PCT/EP98/02461

§ 371 (c)(1),
(2), (4) Date: Aug. 26, 1999

(87) PCT Pub. No.: WO98/48035

PCT Pub. Date: Oct. 29, 1998

(30) Foreign Application Priority Data

Apr. 22, 1997 (EP) .............................. 97201197

(51) Int. Cl.[7] .......................... C12P 35/00; C12P 35/06; C12N 9/00; C12N 9/88; C07H 21/04
(52) U.S. Cl. ............................ 435/47; 435/49; 435/51; 435/183; 435/230; 435/252.3; 435/320.1; 435/935; 435/193; 435/197; 536/23.2; 536/23.74
(58) Field of Search .............................. 435/47, 49, 51, 435/183, 230, 252.3, 320.1, 935, 193, 194; 536/23.2, 23.74

(56) References Cited

U.S. PATENT DOCUMENTS

6,071,713 A * 6/2000 Conder et al. ................. 435/47

FOREIGN PATENT DOCUMENTS

| EP | 0 222 462 B1 | 5/1987 |
| EP | 0 448 180 B1 | 9/1991 |
| WO | WO 95/04149 | 2/1995 |

OTHER PUBLICATIONS

Aharonowitz, Y. et al., "Penicillin and Cephalosporin Biosynthetic Genes: Structure, Organization, Regulation, and Evolution," *Annu Rev. Microbiol* (1992) 46:461–95.

Baldwin, J.E. et al., "Enzymatic Ring Expansion of Penicillins to Cephalosporins: Side Chain Specificity," *J Chem Soc Chem Commun* (Mar. 1, 1987)5:374–375.

Ballio, A. et al., "Incorporation of $\alpha,\omega$–Dicarboxylic Acids as Side–chains into the Penicillin Molecule," *Nature* (Jan. 9, 1960) 185:97–99.

Behrens, O.K. et al., "Biosynthesis of Penicillins I. Biological Precursors for Benzylpenicillin (Penicillin G)," *J Biol Chem* (Sep. 1948) 2:175:751–809.

Cole, M. "Microbial Synthesis of Penicillins," *Process Biochem* (Sep. 1966):334–338.

Ingolia, T.D. et al., "Beta–Lactam Biosynthetic Genes" *Med Res Rev* (1989) 9(2):245–264.

Maeda, K. et al., "The substrate specificity of deacetoxycephalosporin C synthase ("expandase") of *Streptomyces clavuligerus* is extremely narrow," *Enzyme and Microbial Technology* (Mar. 1995) 17:231–234.

* cited by examiner

*Primary Examiner*—Tekchand Saidha
(74) *Attorney, Agent, or Firm*—Morrison & Foerster LLP

(57) ABSTRACT

The present invention disclosures a process for the production of N-deacylated cephalosporin compounds via the fermentative production of their 7-acylated counterparts.

9 Claims, No Drawings

PROCESS FOR THE FERMENTATIVE PRODUCTION OF DEACYLATED CEPHALOSPORINS

FIELD OF THE INVENTION

The present invention relates to the field of fermentative production of N-deacylated cephalosporin compounds, such as 7-ADCA.

BACKGROUND OF THE INVENTION

β-Lactam antibiotics constitute the most important group of antibiotic compounds, with a long history of clinical use. Among this group, the prominent ones are the penicillins and cephalosporins. These compounds are naturally produced by the filamentous fungi *Penicillium chrysogenum* and *Acremonium chrysogenum*, respectively.

As a result of classical strain improvement techniques, the production levels of the antibiotics in *Penicillium chrysogenum* and *Acremonium chrysogenum* have increased dramatically over the past decades. With the increasing knowledge of the biosynthetic pathways leading to penicillins and cephalosporins, and the advent of recombinant DNA technology, new tools for the improvement of production strains and for the in vivo derivatization of the compounds have become available.

Most enzymes involved in β-lactam biosynthesis have been identified and their corresponding genes been cloned, as is decribed by Ingolia and Queener, Med. Res. Rev. 9 (1989), 245–264 (biosynthesis route and enzymes), and Aharonowitz, Cohen, and Martin, Ann. Rev. Microbiol. 46 (1992), 461–495 (gene cloning).

The first two steps in the biosynthesis of penicillin in *P. chrysogenum* are the condensation of the three amino acids L-5-amino-5-carboxypentanoic acid (L-α-aminoadipic acid) (A), L-cysteine (C) and L-valine (V) into the tripeptide LLD-ACV, followed by cyclization of this tripeptide to form isopenicillin N. This compound contains the typical β-lactam structure.

These first two steps in the biosynthesis of penicillins are common in penicillin, cephamycin and cephalosporin producing fungi and bacteria.

The third step involves the exchange of the hydrophilic D-α-aminoadipic acid side chain of isopenicillin N by L-5-amino-5-carboxypentanoic acid, by the action of the enzyme acyltransferase (AT). The enzymatic exchange reaction mediated by AT takes place inside a cellular organelle, the microbody, as has been described in EP-A-0448180.

In cephalosporin-producing organisms, the third step is the isomerization of isopenicillin N to penicillin N by an epimerase, whereupon the five-membered ring structure characteristic of penicillins is expanded by the enzyme expandase to the six-membered ring characteristic of cephalosporins.

The only directly fermented penicillins of industrial importance are penicillin V and penicillin G, produced by adding the hydrophobic side chain precursors phenoxyacetic acid or phenylacetic acid, respectively, during fermentation of *P. chrysogenum*, thereby replacing the side chains of the natural β-lactams with phenoxyacetic acid or phenylacetic acid.

Cephalosporins are much more expensive than penicillins. One reason is that some cephalosporins (e.g. cephalexin) are made from penicillins by a number of chemical conversions. Cephalosporin C, by far the most important starting material in this respect, is very soluble in water at any pH, thus implying lengthy and costly isolation processes using cumbersome and expensive column technology. Cephalosporin C obtained in this way has to be converted into therapeutically used cephalosporins by a number of chemical and enzymatic conversions.

The cephalosporin intermediate 7-ADCA is currently produced by chemical derivatization of penicillin G. The necessary chemical steps to produce 7-ADCA involve the expansion of the 5-membered penicillin ring structure to a 6-membered cephalosporin ring structure.

Recently, fermentative processes have been disclosed to obtain 7-ADCA.

In EP-A-0532341 the application of an adipate (5-carboxypentanoate) feedstock was shown to result in formation of a penicillin derivative with an adipyl side chain, viz. adipyl-6-aminopenicillanic acid. This incorporation is due to the fact that the acyltransferase has a proven wide substrate specificity (Behrens et al., J. Biol. Chem. 175 (1948), 751–809; Cole, Process. Biochem. 1 (1966), 334–338; Ballio et al., Nature 185 (1960), 97–99). In addition, when adipate is fed to a recombinant *P. chrysogenum* strain expressing an expandase, the adipyl-6-APA is expanded to its corresponding cephalosporin derivative. Finally, the removal of the adipyl side chain is suggested, yielding 7-ADCA as a final product.

The patent application EP-A-0540210 describes a similar process for the preparation of 7-ACA, including the extra steps of converting the 3-methyl group of the ADCA ring into the 3-acetoxymethyl group of ACA.

WO95/04148 and WO95/04149 disclose a feedstock of certain thiogroup-containing dicarboxylic acids to an expandase-expressing *P. chrysogenum* strain, resulting in the incorporation of these precursors into the penicillin backbone and subsequent expansion to the corresponding 7-ADCA derivatives.

In general, it is however thought that an expandase that may provide the crucial link between penicillin N and cephalosporin biosynthesis has a narrow specificity (Maea et al., Enzyme and Microbial Technology (1995) 17: 231–234; Baldwin et al., J. Chem. Soc. Chem. Commun. 374–375, 1987), preventing the possibility for catalysing the oxidative ring expansion of penicillin N with unnatural side chains.

The present invention discloses a process for the fermentative production of cephalosporin compounds using novel side chain precursors, which has several advantages above existing processes, advantages with respect to yield and with respect to a decreased level of byproducts.

SUMMARY OF THE INVENTION

The present invention discloses a process for the production of an N-deacylated cephalosporin compound comprising the steps of:

fermenting a microbial strain capable of β-lactam production and expressing acyltransferase as well as expandase activity, and optionally acetyltransferase and/or hydroxylase activity, in the presence of a side chain precursor according to formula (1)

$$HOOC—X—COOH \qquad (1)$$

wherein
X is $(CH_2)_m$—CH=A—$(CH_2)_n$ or $(CH_2)_m$—C≡C—$(CH_2)_n$, wherein
m and n each individually are 0, 1, 2 or 3 and m+n =2 or 3, and A is CH or N, or X is $(CH_2)_p$—CH=CH—CH=C—$(CH_2)_q$, wherein p and q each individually are 0 or 1 and p+q=0 or 1, or a salt, ester or amide thereof, said side chain precursor yielding an acyl-6-APA derivative incorporating said precursor, said acyl-6-APA derivative being in situ expanded to the corresponding acyl-7-ADCA derivative, optionally further reacted to the acyl-7-ADAC or acyl-7-ACA derivative, and recovering the acyl-7-cephalosporin derivative from the fermentation broth deacylating said acyl-7-cephalosporin derivative, and recovering the crystalline N-deacylated cephalosporin compound.

DETAILED DESCRIPTION OF THE INVENTION

The present invention discloses a process for the production of N-deacylated cephalosporin derivatives (7-ADCA, 7-ADAC or 7-ACA) via the fermentative production of their N-acylated counterparts, applying a feed of novel side chain precursors. Using these precursors, novel N-acylated cephalosporin derivatives are formed.

According to the invention, the fermentation of a microbial strain capable of β-lactam production and expressing acyltransferase as well as expandase activity, and optionally hydroxylase or hydroxylase as well as acetyltransferase activity, in the presence of a dicarboxylic acid having one or two unsaturated bonds leads to an improved incorporation of said side chain precursor into the cephalosporin backbone. As a consequence, low levels of undesired acyl-6-APA derivatives are detectable in the process of the invention. In addition, the present invention shows that an improved yield of N-acylated cephalosporin derivative is obtained on an unsaturated precursor as compared to the yield on adipic acid.

The side chain precursor according to the invention has a structure according to formula (1):

$$\text{HOOC—X—COOH} \tag{1}$$

wherein

X is $(CH_2)_m$—CH=A—$(CH_2)_n$ or $(CH_2)_m$—C≡C—$(CH_2)_n$, wherein m and n each individually are 0, 1, 2 or 3 and m+n=2 or 3, and A is CH or N, or X is $(CH_2)_p$—CH=CH—CH=C—$(CH_2)_q$, wherein p and q each individually are 0 or 1 and p+q=0 or 1.

According to the invention, fermentation in the presence of the unsaturated precursor of formula (1), or a salt, ester or amide thereof, produces an acyl-6-APA derivative incorporating said precursor. Said acyl-6-APA derivative subsequently is expanded in situ to the corresponding acyl-7-ADCA derivative.

In particular, the present invention discloses that an acyl-6-APA compound having incorporated the precursor of the invention is an efficient substrate for the subsequent expansion reaction. The amount of the acyl-6-APA product which is formed in the process of the invention is substantially lower than the amount of the byproduct adipyl-6-APA formed in the process for adipyl-7-ADCA production using the side chain precursor adipic acid.

In a preferred embodiment of the invention, a compound according to formula (1) is used as a side chain precursor, wherein m and n are 1 and A is CH. More preferably, the compound according to formula (1) is trans-β-hydromuconic acid. The present invention shows that the acyl-6-APA compound containing a trans-β-muconyl side chain is expanded very efficiently to the corresponding 7-ADCA derivative, since no or only a small amount of 6-APA derivative is detectable. In addition, the yield of N-acylated cephalosporin derivative on this precursor is shown to be improved as compared to the yield on adipic acid.

Microbial strains which are usable in the process of the invention are strains which are capable of β-lactam production and which express acyltransferase as well as expandase activity. Optionally, said microbial strains additionally may express hydroxylase or hydroxylase plus acetyltransferase activity. The former strains enable production of acyl-7-ADCA derivatives, whereas the latter strains enable production of acyl-7-ADAC or acyl-7-ACA derivatives.

Examples of such microbial strains include penicillin-producing strains provided with an expression cassette providing for expandase expression and cephalosporin-producing strains provided with an expression cassette providing for acyltransferase expression.

Expandase genes which conveniently are used may originate from *Acremonium chrysogenum, Streptomyces clavuligerus, Streptomyces antibioticos* or *Nocardia lactamdurans*. The acyltransferase gene may originate from *P. chrysogenum, P. nalgiovense* or *A. nidulans*.

In a preferred embodiment, a penicillin producing fungal strain is used which recombinantly expresses expandase. More preferably, a fungus of the genus Aspergillus or Penicillium is used, most preferably a strain of *Penicillium chrysogenum*. *P. chrysogenum* strain Panlabs P14-B10, DS 18541 (deposited at CBS under accession number 455.95) is an example of a suitable host for expandase expression.

The construction of recombinant expandase-expressing strains is within the knowledge of the skilled person. Examples of expression cassettes which can be used for the construction of recombinant expandase-expressing fungal strains are disclosed in EP-A-0532341, Crawford et al. (Biotechnol. 13 (1995), 58–62) and WO95/04148. Care should be taken to select a transformed strain which has a sufficiently high level of expandase expression. Such transformants can for instance be selected by testing their capacity to produce adipyl-7-ADCA as described by Crawford et al. (supra).

In a different embodiment, a cephalosporin-producing strain is used which recombinantly expresses acyltransferase, for instance an acyltransferase-producing *Acremonium chrysogenum* strain. An *A. chrysogenum* strain recombinantly expressing acyltransferase will thereby produce an acyl-7-ACA derivative, since such a strain natively expresses hydroxylase and acetyltransferase.

These preferred embodiments will contribute enormously to reduce the amount of penicillin by-products, which are not tolerated in the 7-ADCA end product by registration authorities.

The present invention further describes a process for the recovery of an acyl-7-cephalosporin derivative from the fermentation broth of a microbial fermentation according to the invention using specific solvents, e.g. the recovery of an acyl-7-ADCA derivative from the feremnetation broth of an expandase-expressing *P. chrysogenum* strain.

Specifically, the acyl-7-cephalosporin derivative is recovered from the fermentation broth by extracting the broth filtrate with an organic solvent immiscible with water at a pH of lower than about 4.5 and back-extracting the same with water at a pH between 4 and 10.

The broth is filtered and an organic solvent immiscible with water is added to the filtrate. The pH is adjusted in order to extract the acyl-7-cephalosporin derivative from the aqueous layer. The pH range has to be lower than 4.5; preferably between 4 and 1, more preferably between 2 and 1. In this way, the acyl-7-cephalosporin derivative is separated from many other impurities present in the fermentation broth. Preferably a smaller volume of organic solvent is used, e.g. half the volume of solvent relative to the volume of aqueous layer, giving a concentrated solution of the acyl-7-cephalosorin derivative, so achieving reduction of the volumetric flow rates. A second possibility is whole broth extraction at a pH of 4 or lower. Preferably the broth is extracted between pH 4 and 1 with an organic solvent immiscible with water.

Any solvent that does not interfere with the cephalosporin molecule can be used. Suitable solvents are, for instance, butyl acetate, ethyl acetate, methyl isobutyl ketone, alcohols like butanol etc. Preferably 1-butanol or isobutanol are used.

Hereafter, the acyl-7-cephalosporin derivative is back extracted with water at a pH between 4 and 10, preferably between 6 and 9. Again the final volume can be reduced. The recovery can be carried out at temperatures between 0 and 50° C., and preferably at ambient temperatures.

The acyl-7-cephalosporin derivatives produced by the process of the invention are conveniently used as an intermediate for the chemical synthesis of semisynthetic cephalosporins, since the 7-aminogroup is adequately protected by presence of an appropriate acyl side chain.

Alternatively, the acyl-7-cephalosporin derivatives are deacylated in a one-step enzymatical process, using a suitable enzyme, e.g. Pseudomonas SE83 acylase.

Preferably, an immobilized enzyme is used, in order to be able to use the enzyme repeatedly. The methodology for the preparation of such particles and the immobilization of the enzymes have been described extensively in EP-A-0222462. The pH of the aqueous solution has a value of, for example pH 4 to pH 9, at which the degradation reaction of cephalosporin is minimized and the desired conversion with the enzyme is optimized. Thus, the enzyme is added to the aqueous cephalosporin solution while maintaining the pH at the appropriate level by, for instance, adding an inorganic base, such as a potassium hydroxide solution, or applying a cation exchange resin. When the reaction is completed the immobilized enzyme is removed by filtration. Another possibility is the application of the immobilized enzyme in a fixed or fluidized bed column, or using the enzyme in solution and removing the products by membrane filtration. Subsequently, the reaction mixture is acidified in the presence of an organic solvent immiscible with water. After adjusting the pH to about 0.1 to 1.5, the layers are separated and the pH of the aqueous layer is adjusted to 2 to 5. The crystalline cephalosporin compound is then filtered off.

The deacylation can also be carried out chemically as known in the prior art, for instance via the formation of an imino-chloride side chain, by adding phosphorus pentachloride at a temperature of lower than 10° C. and subsequently isobutanol at ambient temperatures or lower.

EXAMPLE 1

Fermentation of Recombinant *P. chrysogenum*

*P. chrysogenum* strain Panlabs P14-B10, deposited at CBS under the accession number 455.95, is used as the host strain for the expandase expression cassette constructs.

The expression cassette used containing the expandase gene under the *P. chrysogenum* IPNS gene transcriptional and translational regulation signals is described in Crawford et al. (supra). Transformation and culturing conditions are as described in Crawford et al. (supra). Transformants are purified and analyzed for expression of the expandase enzyme by testing their capacity to produce adipyl-7-ADCA as described by Crawford et al. (supra).

Acyl-7-ADCA producing transformants are inoculated at 2.106 conidia/ml into a seed medium consisting of (g/l): glucose, 30; Pharmamedia (cotton seed meal), 10; Corn Steep Solids, 20; $(NH_4)_2SO_4$, 20; $CaCO_3$, 5; $KH_2PO_4$, 0,5; lactose, 10; yeast extract, 10 at a pH before sterilisation of 5.6.

The seed culture (20 ml in 250 ml Erlemeyer closed with a cotton plug) is incubated at 25° C. at 220 rpm. After 48 hours, 1 ml was used to inoculate 15 ml of production medium consisting of (g/l): $KH_2PO_4$, 0,5; $K_2SO_4$, 5; $(NH_4)_2SO_4$, 17,5; lactose, 140; Pharmamedia, 20; $CaCO_3$, 10; lard oil, 10 at a pH before sterilisation of 6.6.

After inoculation with the seed culture, a 20% stock solution of the precursor of choice, adjusted to pH 6.5 with KOH, is added to the fermentation to reach a final concentration of 0.5% to 2.0%.

The production culture is cultured at 25° C. and 220 rpm for 168 hours in a 250 ml Erlemeyer flask closed with a milk filter. Evaporated water is replenished every other day.

At the end of the production fermentation, the mycelium is removed by centrifugation or filtration and acyl-6-APA and acyl-7-ADCA are analyzed by HPLC.

EXAMPLE 2

Analysis of Fermentation Products

Fermentation products from transformed Penicillium strains were analyzed by high performance liquid chromatography (HPLC). The HPLC system consisted of the following components: P1000 solvent delivery system (TSP), Autosampler model basic marathon (Spark Holland) (injection volume 3), UV150 (TSP) variable wavelength detector (set at 260 nm) and a PC1000 datasystem (TSP). The stationary phase was a YMC pack ODS AQ 150*4.6 mm column. The mobile phase consisted of 84% phosphate buffer pH 6.0, to which 0.17% tetrabutylammonium hydrogen sulfate has been added, and 16% acetonitril. The products were quantitated by comparison to a standard curve of the expected acyl-7-ADCA.

EXAMPLE 3

Production of N-acylated Penicillin and Cephalosporin Derivatives

A fermentation of *P. chrysogenum* was performed according to Example 1, in the presence of different concentrations of adioic acid (AA) or trans-β-hydromuconic acid (THMA). The N-acylated β-lactam products were analyzed by HPLC according to Example 2.

HPLC analysis revealed that THMA is incorporated in the cephalosporin backbone upon fermentation in the presence of this precursor, i.e. trans-β-hydromuconyl-7-ADCA is formed.

From the results as depicted in Table 1 it further appears that no trans-β-hydromuconyl-6-APA is detectable when fermentation occurred in the presence of THMA. In addition, the yield of trans-β-hydromuconyl-7-ADCA is improved as compared to adipyl-7-ADCA, especially when higher concentrations of the precursor were applied.

TABLE 1

Amount of acyl-6-APA and acyl-7-ADCA formed feeding AA and THMA in different concentrations

| precursor | product formed* | |
|---|---|---|
| | acyl-6-APA | acyl-7-ADCA |
| AA 0.25% | 17 | 72 |
| AA 0.5%. | 25 | 100 |
| AA 1.0% | 25 | 113 |
| AA 2.0% | 30 | 114 |
| THMA 0.25% | nd | 75 |
| THMA 0.5% | nd | 100 |
| THMA 1.0% | nd | 128 |
| THMA 2.0% | nd | 160 |

*Expressed relative to the amount of acyl-7-ADCA formed with a feed of 0.5% adipate, which value is set on 100%
nd = not detectable

What is claimed is:

1. A process for the production of an N-deacylated cephalosporin compound comprising the steps of:

(a) fermenting a microbial strain capable of β-lactam production and expressing acyltransferase as well as expandase activity, and optionally acetyltransferase and/or hydroxylase activity, in the presence of a side chain precursor according to formula (1)

HOOC—X—COOH    (1)

wherein

X is $(CH_2)_m$—CH=A—$(CH_2)_n$ or $(CH_2)_m$—C≡C—$(CH_2)_n$, wherein
   m and n each individually are 0, 1, 2 or 3 and m+n=2 or 3, and
   A is CH or N, or X is $(CH_2)_p$—CH=CH—CH=C—$(CH_2)_q$, wherein
   p and q each individually are 0 or 1 and p+q =0 or 1, or a salt, ester or amide thereof, said side chain precursor yielding an acyl-6-APA derivative incorporating said precursor, said acyl-6-APA derivative being in situ expanded to the corresponding acyl-7-ADCA derivative, optionally further reacted to the acyl-7-ADAC or acyl-7-ACA derivative, and (b) recovering the acyl-7-cephalosporin derivative from the fermentation broth (c) deacylating said acyl-7-cephalosporin derivative, and (d) recovering the crystalline N-deacylated cephalosporin compound.

2. The process of claim 1, wherein an unsaturated side chain precursor of formula (1) is used wherein m and n are 1 and A is CH.

3. The process of claim 2, wherein the unsaturated side chain precursor is trans-β-hydromuconic acid.

4. The process of claim 1, wherein the microbial strain is a penicillin-producing strain provided with an expression cassette providing for expandase expression.

5. The process of claim 4, wherein the penicillin-producing strain is *Penicillium chrysogenum*.

6. The process of claim 4, wherein the crystalline cephalosporin compound is 7-ADCA.

7. The process of claim 1, wherein the microbial strain is a cephalosporin-producing strain provided with an expression cassette providing for acyltransferase expression.

8. The process of claim 7, wherein the cephalosporin-producing strain is *Acremonium chrysogenum*.

9. The process of claim 7, wherein the crystalline cephalosporin compound is 7-ADAC or 7-ACA.

* * * * *